United States Patent
Terao et al.

(10) Patent No.: US 12,070,298 B2
(45) Date of Patent: Aug. 27, 2024

(54) ELECTROCARDIOGRAPH

(71) Applicant: OMRON HEALTHCARE Co., Ltd., Kyoto (JP)

(72) Inventors: Tadahisa Terao, Kyoto (JP); Tomohiro Kukita, Kyoto (JP); Hirotaka Wada, Kyoto (JP); Tamio Ueda, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 717 days.

(21) Appl. No.: 17/175,891

(22) Filed: Feb. 15, 2021

(65) Prior Publication Data

US 2021/0161401 A1 Jun. 3, 2021

Related U.S. Application Data

(63) Continuation of application No. PCT/JP2019/029028, filed on Jul. 24, 2019.

(30) Foreign Application Priority Data

Aug. 21, 2018 (JP) ................................. 2018-154494

(51) Int. Cl.
*A61B 5/0245* (2006.01)
*A61B 5/00* (2006.01)
*A61B 5/08* (2006.01)

(52) U.S. Cl.
CPC .............. *A61B 5/0245* (2013.01); *A61B 5/08* (2013.01); *A61B 5/7405* (2013.01); *A61B 5/742* (2013.01); *A61B 5/7455* (2013.01); *A61B 5/746* (2013.01)

(58) Field of Classification Search
CPC ........... A61B 5/00; A61B 5/308; A61B 5/318; A61B 5/319; A61B 5/0006; A61B 5/332; A61B 5/0245; A61B 5/08
See application file for complete search history.

(56) References Cited

U.S. PATENT DOCUMENTS 5,266,070 A 11/1993 Hagiwara et al.
6,081,742 A 6/2000 Amano et al.
(Continued)

FOREIGN PATENT DOCUMENTS

JP 4-348761 12/1992
JP 7-136142 A 5/1995
(Continued)

OTHER PUBLICATIONS

International Preliminary Report on Patentability issued Feb. 25, 2021 in International (PCT) Patent Application No. PCT/JP2019/029028.
(Continued)

*Primary Examiner* — Paula J Stice
(74) *Attorney, Agent, or Firm* — Wenderoth, Lind & Ponack, L.L.P.

(57) ABSTRACT

An electrocardiograph according to an aspect of the present invention includes an electrocardiographic measurement unit configured to measure electrocardiographic information of a user, a physiological indicator measurement unit configured to measure a physiological indicator of the user, the physiological indicator being different from the electrocardiographic information, a first determination unit configured to determine whether or not the user is in a relaxed state, on the basis of a measurement result of the physiological indicator, and a measurement control unit configured to control the electrocardiographic measurement unit on the basis of a determination result by the first determination unit.

16 Claims, 5 Drawing Sheets

(56) References Cited

U.S. PATENT DOCUMENTS

| | | | |
|---|---|---|---|
| 6,415,174 B1 | 7/2002 | Bebehani et al. | |
| 2005/0197674 A1* | 9/2005 | McCabe | A61N 1/365 607/9 |
| 2008/0082015 A1 | 4/2008 | Kohls et al. | |
| 2013/0144130 A1* | 6/2013 | Russell | A61B 5/335 600/301 |
| 2017/0258349 A1 | 9/2017 | Watanabe | |
| 2018/0338698 A1 | 11/2018 | Yoshimura | |

FOREIGN PATENT DOCUMENTS

| | | |
|---|---|---|
| JP | 2008-86770 | 4/2008 |
| JP | 2014-226367 A | 12/2014 |
| JP | 2016-047092 | 4/2016 |
| JP | 2017-29339 | 2/2017 |
| WO | 98/10699 | 3/1998 |
| WO | 2017/145363 A1 | 8/2017 |

OTHER PUBLICATIONS

Haruaki Nakaya, "Atria-selective antiarrhythmic drugs" Journal of Clinical and Experimental Medicine, vol. 234, No. 6, Aug. 7, 2010, pp. 655-660.

Notice of Reasons for Refusal issued Jul. 26, 2022 in corresponding Japanese Patent Application No. 2018-154494 with machine translation.

\* cited by examiner

[FIG. 1]
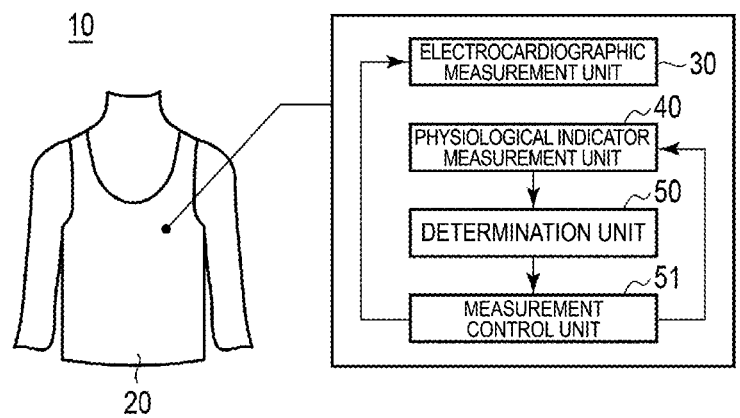
[FIG. 2]
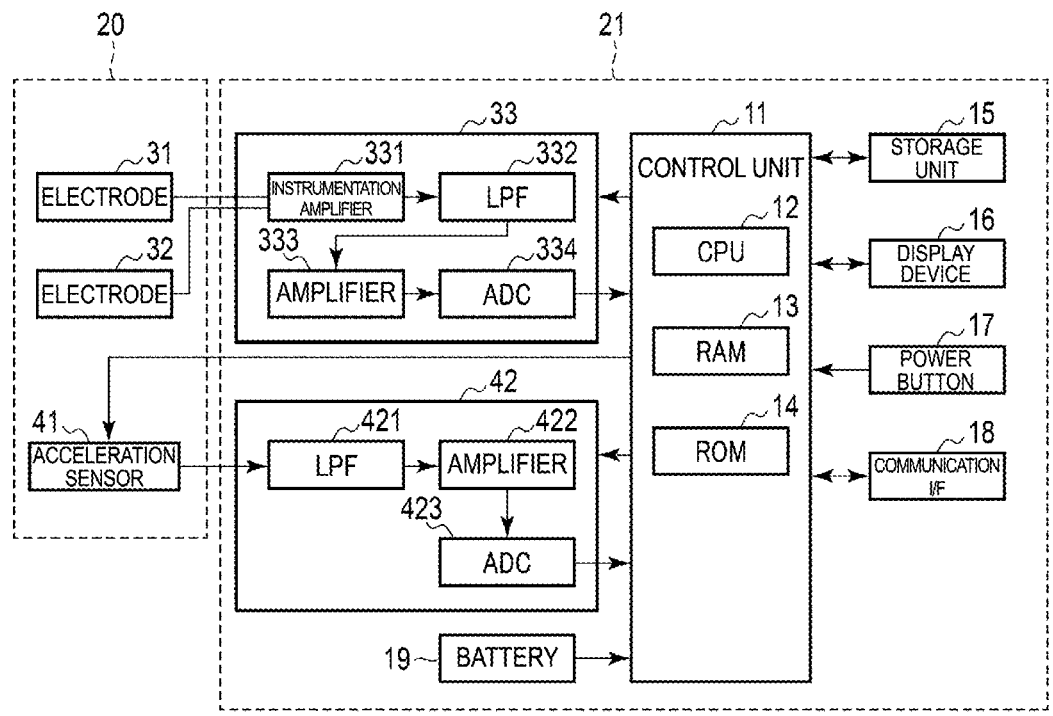

[FIG. 3]
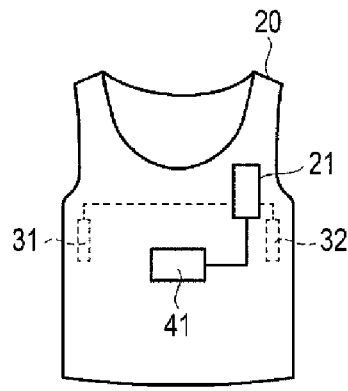
[FIG. 4]
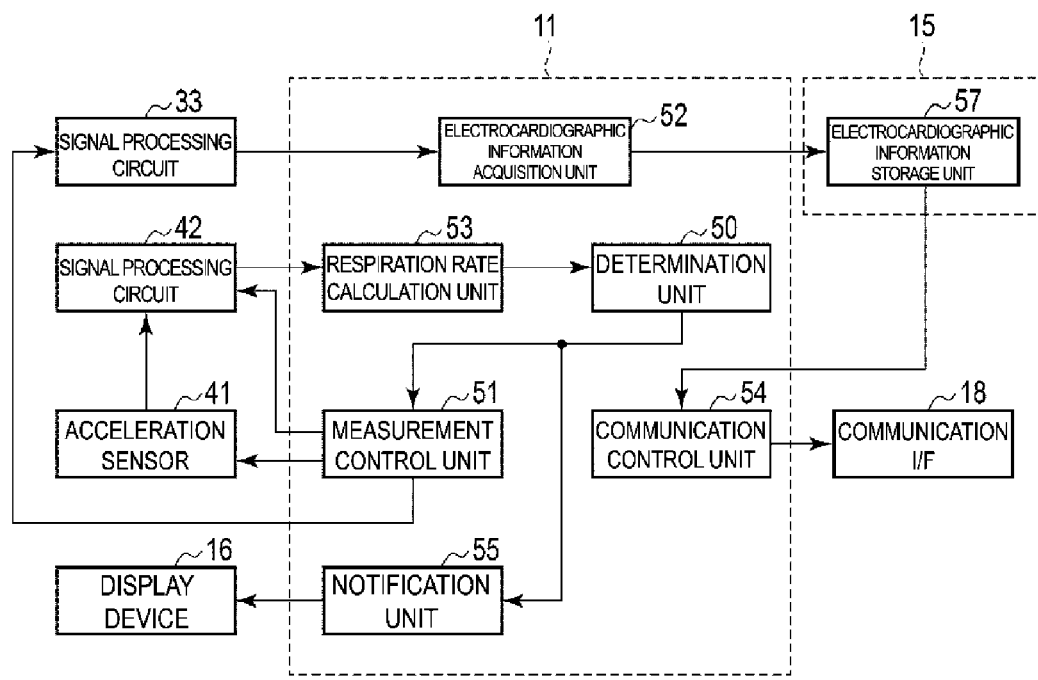

[FIG. 5]
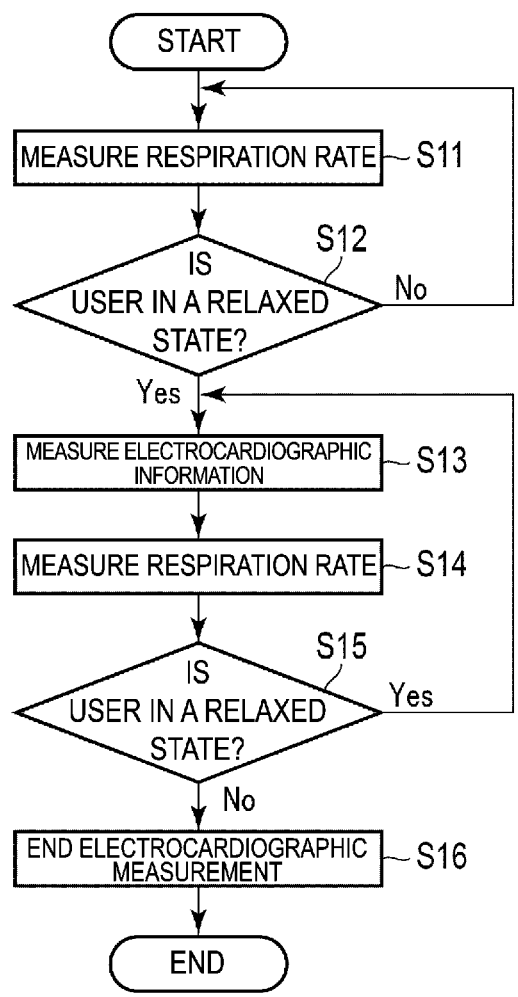

[FIG. 6]
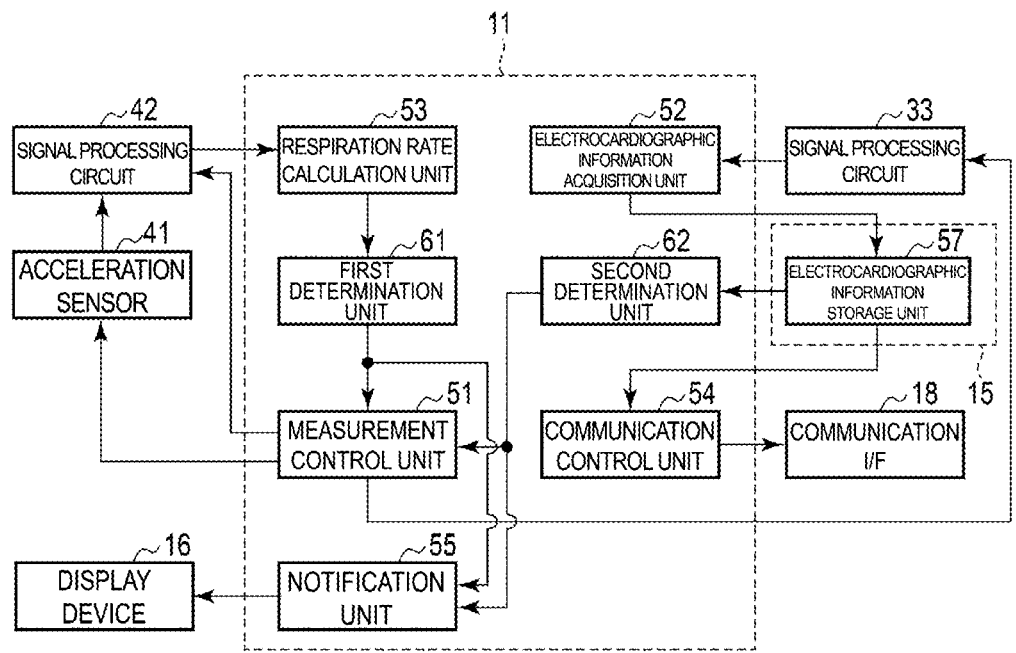
[FIG. 7]
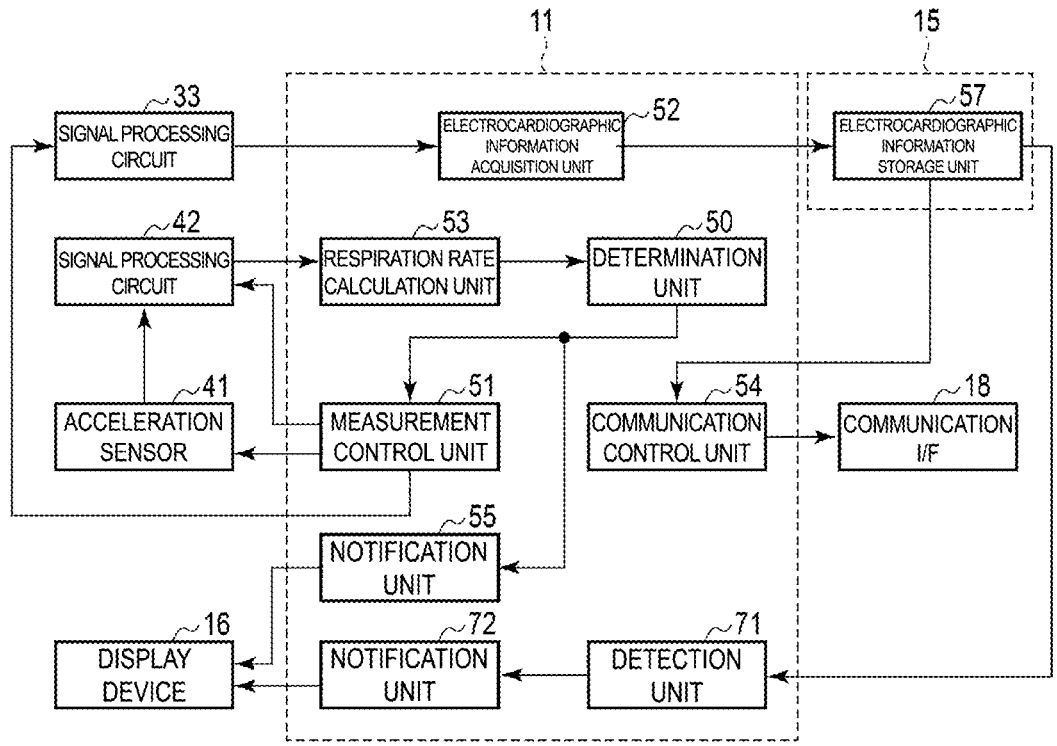

[FIG. 8]
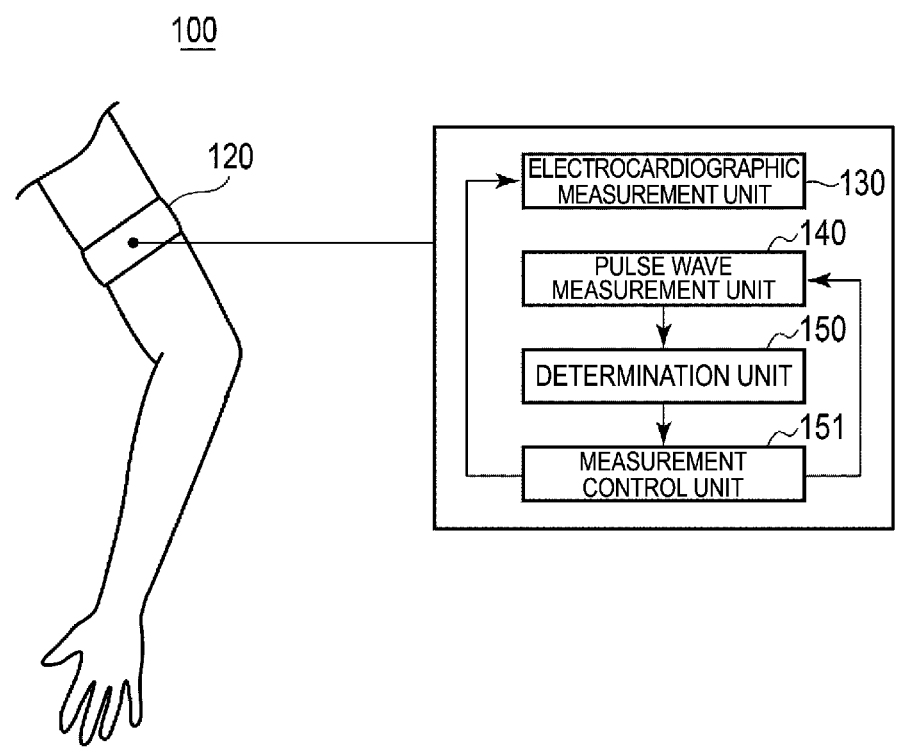

ELECTROCARDIOGRAPH

CROSS-REFERENCE TO RELATED APPLICATIONS

This application is the U.S. national stage application filed pursuant to 35 U.S.C. 365(c) and 120 as a continuation of International Patent Application No. PCT/JP2019/029028, filed Jul. 24, 2019, which application claims priority from Japanese Patent Application No. 2018-154494, filed Aug. 21, 2018, which applications are incorporated herein by reference in their entireties.

TECHNICAL FIELD

One aspect of the present invention relates to a portable electrocardiograph, for example.

BACKGROUND ART

To perform an examination regarding heart diseases such as atrial fibrillation, typically electrocardiographic information of a patient is measured over an extended period of time (e.g. 24 hours) using a portable electrocardiograph, such as a Holter electrocardiograph. To reduce a burden on the patient caused by attaching the electrocardiograph, an electrocardiograph in the form of a garment such as a shirt has been developed (see, for example, Patent Document 1).

CITATION LIST

Patent Literature

Patent Document 1: JP 2014-226367 A

SUMMARY OF INVENTION

Technical Problem

In portable electrocardiographs, there is a demand to be able to reduce power consumption while collecting data of electrocardiographic information necessary for the examination regarding heart disease.

The present invention has been made with reference to the above circumstances, and an object of an aspect of the present invention is to provide an electrocardiograph that is capable of power saving.

Solution to Problem

The present invention adopts the following configurations in order to solve the above problems, for example.

An electrocardiograph according to an aspect includes an electrocardiographic measurement unit configured to measure electrocardiographic information of a user, a physiological indicator measurement unit configured to measure a physiological indicator of the user, the physiological indicator being different from the electrocardiographic information, a first determination unit configured to determine whether or not the user is in a relaxed state, on the basis of a measurement result of the physiological indicator, and a measurement control unit configured to control the electrocardiographic measurement unit on the basis of a determination result by the first determination unit.

Certain abnormalities in the heart, such as atrial fibrillation, are known to be prone to occur when the user is relaxing. The relaxed state refers to the condition in which the parasympathetic nerves are predominately working, or the parasympathetic nerves are estimated to be working predominately. According to the above-described configuration, the measurement of the electrocardiographic information is started when the user is determined to be in the relaxed state. This allows the electrocardiographic information to be measured when the user is in the relaxed state.

As a result, the power consumption can be reduced while acquiring data of electrocardiographic information necessary for an examination regarding cardiac abnormalities, such as atrial fibrillation.

In another aspect, the physiological indicator may be respiration rate, and the first determination unit may be configured to determine that the user is in the relaxed state in a case where the respiration rate is below a preset threshold and determine that the user is not in the relaxed state in a case where the respiration rate exceeds the threshold.

According to the above-described configuration, threshold processing on the measurement result of respiration rate is used to determine whether or not the user is in the relaxed state. Thus, the determination processing can be made simple, and the power consumed in the determination processing is reduced.

In another aspect, the measurement control unit may be configured to, in response to the first determination unit determining that the user is in the relaxed state, control the electrocardiographic measurement unit to start measuring the electrocardiographic information and, in response to the first determination unit determining that the user is not in the relaxed state, control the electrocardiographic measurement unit to stop measuring the electrocardiographic information.

According to the above-described configuration, it is possible to measure the electrocardiographic information when the user is in the relaxed state, and not to measure the electrocardiographic information when the user is not in the relaxed state.

Thus, the power consumption can be reduced while acquiring data of electrocardiographic information necessary for an examination regarding cardiac abnormalities, such as atrial fibrillation, which are prone to occur when the user is in the relaxed state.

In another aspect, the measurement control unit may be configured to control the physiological indicator measurement unit to continuously measure the physiological indicator in a time period in which the electrocardiographic measurement unit is not measuring the electrocardiographic information.

According to the above-described configuration, it is possible to quickly detect that the user has entered the relaxed state, compared to a configuration in which the physiological indicator is measured periodically.

In another aspect, the electrocardiograph may further include a second determination unit configured to determine whether or not the user is in the relaxed state, on the basis of a measurement result of the electrocardiographic information, and the measurement control unit may be configured to, in response to the first determination unit determining that the user is in the relaxed state, control the electrocardiographic measurement unit to start measuring the electrocardiographic information and, in response to the second determination unit determining that the user is not in the relaxed state, control the electrocardiographic measurement unit to stop measuring the electrocardiographic information.

According to the above-described configuration, it is determined whether the user is in a relaxed state, based on a measurement result of the electrocardiographic information during measurement of the electrocardiographic information. Therefore, there is no need to drive the physiological indicator measurement unit during measurement of the electrocardiographic information. As a result, power consumption can be reduced.

In another aspect, the electrocardiograph may further include a communication control unit configured to transmit a measurement result of the electrocardiographic information to an external device.

According to the above-described configuration, the amount of data of the electrocardiographic information is reduced, and thus, the power consumed to transmit the data of the electrocardiographic information is reduced.

In another aspect, the electrocardiograph may further include a first notification unit configured to notify the user of a determination result by the first determination unit.

According to the above-described configuration, the user can be informed that the user is not in the relaxed state. As a result, the user can be prompted to enter relaxed state.

In another aspect, the electrocardiograph may further include a second notification unit, and the physiological indicator measurement unit may be configured to measure a plurality of types of physiological indicators of the user, the plurality of types of physiological indicators being different from the electrocardiographic information, the first determination unit may be configured to, in a case where the first determination unit determines that the user is not in the relaxed state, generate determination information indicating a type of physiological indicator, from among the plurality of types of physiological indicators, being the cause of determination that the user is not in the relaxed state, and the second notification unit may be configured to notify the user of the type of physiological indicator, indicated by the determination information, being the cause of determination that the user is not in the relaxed state.

According to the above-described configuration, a user can be informed of the cause of why the user was determined to not be in the relaxed state. As a result, the user can be prompted to enter relaxed state.

Advantageous Effects of Invention

According to the present invention, an electrocardiograph capable of power saving can be provided.

BRIEF DESCRIPTION OF DRAWINGS

FIG. 1 is a diagram schematically illustrating an electrocardiograph according to an embodiment.

FIG. 2 is a block diagram illustrating a hardware configuration of the electrocardiograph illustrated in FIG. 1.

FIG. 3 is a diagram illustrating the appearance of the electrocardiograph illustrated in FIG. 1.

FIG. 4 is a block diagram illustrating a software configuration of the electrocardiograph illustrated in FIG. 1.

FIG. 5 is a flowchart illustrating a method for measuring electrocardiographic information executed by the electrocardiograph illustrated in FIG. 1.

FIG. 6 is a block diagram illustrating a software configuration of an electrocardiograph according to an embodiment.

FIG. 7 is a block diagram illustrating a software configuration of an electrocardiograph according to an embodiment.

FIG. 8 is a diagram schematically illustrating an electrocardiograph according to an embodiment.

DESCRIPTION OF EMBODIMENTS

Hereinafter, an embodiment of the present invention will be described with reference to the drawings.

Application Example

With reference to FIG. 1, an example of a case to which the present invention is applied will be described. FIG. 1 illustrates an example of a portable electrocardiograph 10 according to an embodiment. The electrocardiograph 10 is configured to be attached to a user, for example. The electrocardiograph 10 includes an attachment member 20, an electrocardiographic measurement unit 30, a respiration rate measurement unit 40, a determination unit 50, and a measurement control unit 51.

In the example of FIG. 1, the attachment member 20 is configured as a shirt worn on an upper body of a user and is used to attach the electrocardiograph 10 to a user.

The electrocardiographic measurement unit 30 measures the electrocardiographic information of the user. The respiration rate measurement unit 40 measures the respiration rate of the user. The respiration rate is the number of breaths per unit time. The respiration rate measurement unit 40 is an example of a physiological indicator measurement unit that measures a physiological indicator of a user which is different from the electrocardiographic information. The physiological indicator is an indicator associated with a biological information of the user. As described below, the measurement result of the physiological indicator is used to determine whether or not the user is in a relaxed state. Thus, the physiological indicator that is measured by the physiological indicator measurement unit is able to be used to determine whether or not the user is in a relaxed state and, for example, is respiration rate, pulse, heart rate, pulse wave, or the like. The relaxed state refers to the condition in which the parasympathetic nerves are predominately working, or the parasympathetic nerves are estimated to be working predominately.

The determination unit 50 determines whether or not the user is in the relaxed state on the basis of the measurement result of the respiration rate output from the respiration rate measurement unit 40. Specifically, the determination unit 50 determines that the user is in the relaxed state in a case where the respiration rate is below a preset threshold and determines that the user is not in the relaxed state in a case where the respiration rate exceeds the threshold.

The measurement control unit 51 controls the electrocardiographic measurement unit 30 and the respiration rate measurement unit 40. The measurement control unit 51 controls the electrocardiographic measurement unit 30 on the basis of the result of the determination by the determination unit 50. As an example, the measurement control unit 51 controls the respiration rate measurement unit 40 so as to periodically perform the measurement and, in response to the determination unit 50 determining that the user is in the relaxed state, controls the electrocardiographic measurement unit 30 to start measuring electrocardiographic information and, in response to the determination unit 50 determining that the user is not in the relaxed state, controls the electrocardiographic measurement unit 30 to stop measuring electrocardiographic information.

According to the electrocardiograph 10 having the configuration described above, when the user is in the relaxed state, the electrocardiographic information is measured, and when the user is not in the relaxed state, the electrocardiographic information is not measured. Certain abnormalities in the heart, such as atrial fibrillation, are known to be prone to occur when the user is relaxing (when parasympathetic nerves are dominant). Accordingly, the electrocardiograph 10 is controlled to measure electrocardiographic information when atrial fibrillation is prone to occur. Thus, the power consumption can be reduced while acquiring data of electrocardiographic information necessary for an examination regarding cardiac abnormalities, such as atrial fibrillation.

Next, the electrocardiograph 10 will be described in detail.

Configuration Example

Hardware Configuration

An example of the hardware configuration of the electrocardiograph 10 will be described with reference to FIGS. 2 and 3. In the example of FIG. 2, the electrocardiograph 10 includes a control unit 11, a storage unit 15, a display device 16, a power button 17, a communication interface 18, a battery 19, the attachment member 20, a case 21, electrodes 31 and 32, a signal processing circuit 33, an acceleration sensor 41, and a signal processing circuit 42. As illustrated in FIG. 3, the case 21, the electrodes 31 and 32, and the acceleration sensor 41 are provided in the attachment member 20. The control unit 11, the storage unit 15, the display device 16, the power button 17, the communication interface 18, the battery 19, the signal processing circuit 33, and the signal processing circuit 42 are provided in the case 21.

Referring to FIG. 2, the control unit 11 includes a central processing unit (CPU) 12, a random access memory (RAM) 13, a read only memory (ROM) 14, and the like and controls each constituent element. For example, the storage unit 15 is an auxiliary storage device such as a semiconductor memory (for example, a flash memory) and stores, in a non-volatile manner, programs executed by the control unit 11, settings data necessary for executing the programs, electrocardiographic information measurement data, and the like. A storage medium included in the storage unit 15 is a medium that accumulates information such as a program by electrical, magnetic, optical, mechanical, or chemical action so that a computer, a machine, or the like can read the information such as the program being recorded. Note that at least one or all of the programs may be stored in the ROM 14.

The display device 16 includes, for example, one or more light emitting diode (LED) lamps that indicate an operating state. For example, the display device 16 includes an LED lamp that indicates whether or not power is on, an LED lamp that indicates whether or not a communication is possible state, and an LED lamp that indicates the determination result of whether or not the user is in the relaxed state. Note that the display device 16 may include an image display device such as a liquid crystal display device. The power button 17 is a button for switching the power on and off.

The communication interface 18 is an interface for communicating with an external device (for example, a smart phone of the user). Typically, the communication interface 18 includes a wireless module compliant with a low power wireless communication protocol such as Bluetooth (trade name).

The battery 19 supplies power to each of the constituent elements. Specifically, the battery 19 supplies power to the control unit 11, the storage unit 15, the display device 16, the communication interface 18, the signal processing circuit 33, the acceleration sensor 41, and the signal processing circuit 42. The battery 19 may be a rechargeable battery.

Referring to FIG. 3, the electrodes 31 and 32 are provided on the inner circumferential surface of the attachment member 20. The inner circumferential surface of the attachment member 20 refers to a portion of the surface of the attachment member 20 that faces the user in a state where the electrocardiograph 10 is attached to the user (hereinafter, simply referred to as an attachment state). In the attachment state, the electrodes 31 and 32 come into contact with the body surface of the user. The electrodes 31 and 32 are disposed on the attachment member 20 such that the heart of the user is located between the electrodes 31 and 32 in the attachment state. The electrodes 31 and 32 are formed using, for example, a fiber impregnated with an electrically conductive polymer. The electrodes 31 and 32 are connected to the signal processing circuit 33.

Referring to FIG. 2, the signal processing circuit 33 includes an instrumentation amplifier 331, a low pass filter (LPF) 332, an amplifier 333, and an analog-to-digital converter (ADC) 334. The instrumentation amplifier 331 includes two input terminals, and the electrodes 31 and 32 are respectively connected to the input terminals. The instrumentation amplifier 331 performs differential amplification on the potential of the electrode 31 and the potential of the electrode 32, and generates a potential difference signal in accordance with the potential difference between the electrode 31 and the electrode 32. The instrumentation amplifier 331 is an example of a potential difference signal generation unit that generates a potential difference signal indicating the potential difference between the electrode 31 and the electrode 32. The potential difference signal is filtered by the LPF 332, amplified by the amplifier 333, and converted into a digital signal by the ADC 334. The control unit 11 acquires, as the electrocardiographic information measurement result, the potential difference signal output in a time series from the signal processing circuit 33. The electrocardiographic information is a waveform signal that indicates the electrical activity of the heart of the user. In this example, the electrodes 31 and 32, the signal processing circuit 33, and the control unit 11 constitute the electrocardiograph measurement unit 30 illustrated in FIG. 1.

Note that the arrangement of the electrodes 31 and 32 is not limited to the example illustrated in FIG. 3. Furthermore, three or more electrodes may be provided on the inner circumferential surface of the attachment member 20, and the electrocardiographic information may be measured using these electrodes.

Referring to FIG. 3, the acceleration sensor 41 is provided on a portion of the attachment member 20 corresponding to the chest. The acceleration sensor 41 is, for example, a triaxial acceleration sensor and generates an acceleration signal representing acceleration in three directions orthogonal to each other. The output of the acceleration sensor 41 is connected to the signal processing circuit 42.

Referring to FIG. 2, the signal processing circuit 42 includes an LPF 421, an amplifier 422, and an ADC 423. The acceleration signal is filtered by the LPF 421, amplified by the amplifier 422, and converted into a digital signal by the ADC 423. The control unit 11 measures the respiration rate on the basis of the acceleration signal output in a time series from the signal processing circuit 42. In this example, the acceleration sensor 41, the signal processing circuit 42, and the control unit 11 constitute the respiration rate measurement unit 40 illustrated in FIG. 1.

Note that other sensors such as a strain gauge or a piezoelectric sensor may be used instead of the acceleration sensor 41.

Note that, with regard to a specific hardware configuration of the electrocardiograph 10, constituent elements can be omitted, replaced, and added as appropriate according to the embodiment. For example, the control unit 11 may include a plurality of processors.

Software configuration

With reference to FIG. 4, an example of a software configuration of the electrocardiograph 10 will be described. In the example illustrated in FIG. 4, the electrocardiograph 10 includes the determination unit 50, the measurement control unit 51, an electrocardiographic information acquisition unit 52, a respiration rate calculation unit 53, a communication control unit 54, a notification unit 55, and an electrocardiographic information storage unit 57. The determination unit 50, the measurement control unit 51, the electrocardiographic information acquisition unit 52, the respiration rate calculation unit 53, the communication control unit 54, and the notification unit 55 execute the following processing by the control unit 11 of an electrocardiograph 10 executing a program stored in the storage unit 15. When the control unit 11 executes the program, the control unit 11 deploys the program in the RAM 13. Then, the control unit 11 causes the CPU 12 to interpret and execute the program deployed in the RAM 13 to control each of the constituent elements. The electrocardiographic information storage unit 57 is realized by the storage unit 15.

The electrocardiographic information acquisition unit 52 acquires, as the electrocardiographic information, a potential difference signal indicating the potential difference between the electrode 31 and the electrode 32 output in a time series from the signal processing circuit 33, and stores the data of the electrocardiographic information in the electrocardiographic information storage unit 57.

The respiration rate calculation unit 53 calculates the respiration rate on the basis of the acceleration signal output in a time series from the signal processing circuit 42. A known technique can be used as the method for calculating the respiration rate on the basis of the acceleration signal, and thus detailed descriptions thereof will be omitted.

The determination unit 50 determines whether or not the user is in the relaxed state on the basis of the respiration rate calculated by the respiration rate calculation unit 53. For example, the determination unit 50 determines that the user is in the relaxed state in a case where the respiration rate is below a preset threshold and determines that the user is not in the relaxed state in a case where the respiration rate exceeds the threshold. The respiration rate is defined, for example, as the number of breaths per minute. The threshold is, for example, 13.5 (times/min).

The measurement control unit 51 controls the signal processing circuit 33, the acceleration sensor 41, and the signal processing circuit 42. The measurement control unit 51 controls the operation of the acceleration sensor 41 and the signal processing circuit 42 in order to periodically measure the respiration rate. For example, the measurement control unit 51 repeats the process of driving the acceleration sensor 41 and the signal processing circuit 42 for one minute and then deactivating the acceleration sensor 41 and the signal processing circuit 42 for 14 minutes. As a result, the respiration rate is measured in a 15 minute period, and the determination unit 50 determines on the basis of the measurement result of the respiration rate.

In response to the determination unit 50 determining that the user is in the relaxed state, the measurement control unit 51 drives the signal processing circuit 33, and in response to the determination unit 50 determining that the user is not in the relaxed state, the measurement control unit 51 stops the signal processing circuit 33. The electrocardiographic information is measured during a period in which the signal processing circuit 33 is driven.

The communication control unit 54 controls the communication interface 18. For example, the communication control unit 54 reads the data of the electrocardiographic information from the electrocardiographic information storage unit 57 and transmits the data of the electrocardiographic information to an external device via the communication interface 18.

The notification unit 55 notifies the user of the result of the determination by the determination unit 50, for example, via the display device 16. For example, the LED lamp indicating the determination result included in the display device 16 emits blue when the user is in the relaxed state and emits red when the user is not in the relaxed state. Note that the LED lamp may emit light only when the user is not in the relaxed state. The notification unit 55 corresponds to a "first notification unit" of the present invention.

Note that, in the present embodiment, the example in which any of the functions of the electrocardiograph 10 is realized by a general-purpose processor is described. However, some or all of the functions may be implemented by one or more dedicated processors.

Operation Example

FIG. 5 illustrates an example of an operation flow when the electrocardiograph 10 measures electrocardiographic information.

In step S11 of FIG. 5, the control unit 11 measures the respiration rate of the user. Specifically, the control unit 11 operates as the respiration rate calculation unit 53 and calculates the respiration rate of the user based on the output of the acceleration sensor 41. The measurement of the respiration rate is performed periodically.

In step S12, the control unit 11 functions as the determination unit 50 and determines whether or not the user is in the relaxed state based on the measurement result of the respiration rate. Specifically, the control unit 11 determines that the user is in the relaxed state in the case where the respiratory rate is below a threshold, and otherwise determines that the user is not in the relaxed state. In a case where the control unit 11 determines that the user is in the relaxed state, the process proceeds to step S13, and in a case where the control unit 11 determines that the user is not in the relaxed state, the process returns to step S11.

In step S13, the control unit 11 measures the electrocardiographic information of the user. Specifically, the control unit 11 functions as the measurement control unit 51 and drives the signal processing circuit 33. Then, the control unit 11 functions as the electrocardiographic information acquisition unit 52, acquires, as the electrocardiographic information, a potential difference signal indicating the potential difference between the electrode 31 and the electrode 32 output from the signal processing circuit 33, and stores in the electrocardiographic information storage unit 57.

In step S14, the control unit 11 measures the respiration rate of the user. As described above, the measurement of the respiration rate is performed periodically. Accordingly, the measurement of the respiration rate is performed even during measurement of the electrocardiographic information.

In step S15, the control unit 11 functions as the determination unit 50 and determines whether or not the user is in the relaxed state based on the measurement result of the respiration rate. In a case where the control unit 11 determines that the user is in the relaxed state, the process returns to step S13, and in a case where the control unit 11 determines that the user is not in the relaxed state, the process proceeds to step S16.

In step S16, the control unit 11 finishes measuring the electrocardiographic information. Specifically, the control unit 11 functions as the measurement control unit 51 and stops the signal processing circuit 33. Then, the process returns to step S11. The process from step S11 to step S16 is repeated until the power is turned off In this way, the control unit 11 measures the electrocardiographic information of the user in a period from when it is determined that the user is in the relaxed state until when it is determined that the user is not in the relaxed state.

Furthermore, the process procedure illustrated in FIG. 5 is merely an example and the process procedure and contents thereof can be appropriately changed. For example, the control unit 11 may operate as the communication control unit 54 and transmit the data of the electrocardiographic information obtained in step S13 to the external device in real-time.

The control unit 11 can operate as the notification unit 55. For example, the control unit 11 may turn on the LED lamp that indicates the determination result in red until it is determined that the user is in the relaxed state in step S12. The control unit 11 may turn on the LED that indicates the determination result in blue from when it is determined that the user is in the relaxed state in step S12 until when it is determined that the user is not in the relaxed state step S15. The control unit 11 may turn on the LED lamp that indicates the determination result in red when it is determined that the user is not in the relaxed state in step S15.

Effects

As described above, the electrocardiograph 10 measures the respiration rate of the user and determines whether or not the user is in the relaxed state based on the measurement result of the respiration rate. Then, in a case where it is determined that the user is in the relaxed state, the electrocardiograph 10 starts measuring the electrocardiographic information and, in a case where it is determined that the user is not in the relaxed state, stops measuring the electrocardiographic information. In this manner, it is possible to make the electrocardiographic information to be measured in a time period in which atrial fibrillation is prone to occur, and the electrocardiographic information not measured in other time periods. As a result, data of the electrocardiographic information required for examination regarding atrial fibrillation can be collected while reducing power consumption. Because the amount of data of the electrocardiographic information is reduced, the power consumed to wirelessly transmit the data of the electrocardiographic information can be reduced.

Determination of whether the user is in the relaxed state is performed by threshold processing using the measurement result of the respiration rate. The determination processing can be made simple, and thus the power consumed in the determination processing can be reduced.

Furthermore, the determination result of whether or not the user is in the relaxed state is notified to the user. This allows the user to be informed that the user is not in the relaxed state. As a result, the user can be prompted to enter relaxed state so that the measurement of the electrocardiographic information is not insufficient.

Modified Examples

Note that the present invention is not limited to the embodiments described above.

In the embodiment described above, the measurement of the respiration rate is performed periodically. In one or more embodiments, the measurement of respiration rate may be performed continuously. In other words, the respiration rate of the user may be constantly monitored. In one or more embodiments, the measurement of the respiration rate may be performed continuously when measurement of the electrocardiographic information is not taking place, and the measurement of the respiration rate may be performed periodically during measurement of the electrocardiographic information. These embodiments are capable of quickly detecting that the user has entered the relaxed state. As a result, the reliability of measuring the electrocardiographic information when the user is in the relaxed state is improved.

In one or more embodiments, the electrocardiograph 10 may measure a plurality of types of physiological indicators that are different from the electrocardiographic information and determine whether or not the user is in the relaxed state based on the measurement results. In a case where the control unit 11 determines that the user is not in the relaxed state, the control unit 11 may generate determination information indicating a type of a physiological indicator, from among the plurality of types of physiological indicators, which is the cause of determination that the user is not in the relaxed state. The control unit 11 may operates as a second notification unit, and may notify the user, for example, via the display device 16, of the type of physiological indicator, indicated by the determination information, which is the cause of determination that the user is not in the relaxed state. The notification may be made by changing the color of the LED lamp. In a case where the display device 16 includes an image display device, the control unit 11 may display, on the image display device, a character string identifying the type of physiological indicator that is the cause of determination that the user is not in the relaxed state. This allows the user to be informed of the cause of determination that the user is not in the relaxed state. As a result, the user can be prompted to enter relaxed state. For example, in a case where the user realizes that the respiration rate is the cause why the user is not in the relaxed state, the user can perform deep breathing or other such actions to enter the relaxed state.

In one or more embodiments, during measurement of the electrocardiographic information, whether or not the user is in the relaxed state may be determined on the basis of the measurement result of the electrocardiographic information. This embodiment will be simply described with reference to FIG. 6.

FIG. 6 illustrates an example of the software configuration of an electrocardiograph according to one or more embodiments. In the example illustrated in FIG. 6, the electrocardiograph includes the measurement control unit 51, the electrocardiographic information acquisition unit 52, the respiration rate calculation unit 53, the communication control unit 54, the notification unit 55, a first determination unit 61, a second determination unit 62, and the electrocardiographic information storage unit 57. In FIG. 6, elements similar to those illustrated in FIG. 4 are given the same reference signs, and descriptions thereof will be omitted as appropriate. The measurement control unit 51, the electrocardiographic information acquisition unit 52, the respiration rate calculation unit 53, the communication control unit 54, the notification unit 55, the first determination unit 61, and the second determination unit 62 execute predetermined processing by the control unit of an electrocardiograph executing a program stored in the storage unit.

The first determination unit 61 corresponds to the determination unit 50 illustrated in FIG. 4. Specifically, the first determination unit 61 determines that the user is in the relaxed state in a case where the respiration rate calculated by the respiration rate calculation unit 53 is below a preset threshold, and determines that the user is not in the relaxed state in a case where the respiration rate exceeds the threshold.

The second determination unit 62 determines whether or not the user is in the relaxed state based on the electrocardiographic information acquired by the electrocardiographic information acquisition unit 52. Specifically, the second determination unit 62 calculates an R-R Interval (RRI), which is an interval between adjacent R waves, from the electrocardiographic information, and generates time series data of RRI. Next, the second determination unit 62 calculates the power spectral density from the time series data of RRI using the autoregressive model, calculates the integrated value of power over the frequency range from 0.05 Hz to 0.15 Hz as LF, and calculates the integrated value of power over the frequency range from 0.15 Hz to 0.40 Hz as HF. LF/HF, which is the LF to HF ratio, represents a balance between sympathetic and parasympathetic nerves, with a higher value indicating a sympathetic nerve dominance and a lower value indicating a parasympathetic nerve dominance. The second determination unit 62 determines that the user is in the relaxed state in a case where the LF/HF is below a preset threshold, and determines that the user is not in the relaxed state in a case where the LF/HF is equal to or greater than the threshold.

Based on the result of the determination made by the first determination unit 61 and the result of the determination by the second determination unit 62, the notification unit 55 notifies the user of the determination result of whether or not the user is in the relaxed state.

Note that the second determination unit 62 may calculate the heart rate from the electrocardiographic information, and may determine that the user is in the relaxed state in a case where the calculated heart rate value is below a preset threshold and determine that the user is not in the relaxed state in a case where the calculated heart rate value exceeds the threshold. The heart rate refers to the number of times of the heart beats per unit time.

The first determination unit 61 operates when the measurement of the electrocardiographic information is not being performed, and the second determination unit 62 operates during measurement of the electrocardiographic information. In this case, there is no need to measure the respiration rate during measurement of the electrocardiographic information. In other words, during measurement of the electrocardiographic information, it is not necessary to drive the signal processing circuit 42, and no processing is performed by the respiration rate calculation unit 53. In this manner, power consumption can be reduced.

In one or more embodiments, the electrocardiograph 10 may further include a detection unit 71 and a notification unit 72, as illustrated in FIG. 7. The detection unit 71 and the notification unit 72 execute the following processing by the control unit 11 of the electrocardiograph 10 executing a program stored in the storage unit 15.

The detection unit 71 detects that atrial fibrillation has occurred in the heart of the user, on the basis of the electrocardiographic information acquired by the electrocardiographic information acquisition unit 52. The notification unit 72 notifies the user in response to the detection unit 71 detecting that atrial fibrillation has occurred. The notification can be performed by sound, light, vibration, or the like. This allows the user to realize that atrial fibrillation has occurred.

In the embodiment described above, the respiration rate is adopted as a physiological indicator different from the electrocardiographic information. In one or more embodiments, a pulse wave may be adopted as a physiological indicator.

FIG. 8 illustrates an example of the electrocardiograph 100 according to an embodiment. In the example of FIG. 8, the electrocardiograph 100 is configured to be attached to the upper arm of a user. The electrocardiograph 100 includes an attachment member 120, an electrocardiographic measurement unit 130, a pulse wave measurement unit 140, a determination unit 150, and a measurement control unit 151.

The attachment member 120 is a member that is wound around the upper arm of the user, and has a band, belt, or roll shape. The electrocardiographic measurement unit 130, the pulse wave measurement unit 140, the determination unit 150, and the measurement control unit 151 are provided in the attachment member 120.

The electrocardiographic measurement unit 130 measures the electrocardiographic information of the user. The electrocardiographic measurement unit 130 includes at least two electrodes on an inner circumferential surface of the attachment member 120, and the electrocardiographic information is measured using these electrodes. In the attachment state, the electrodes come into contact with the skin of the upper arm of the user. It is generally known that electrocardiographic information can be measured using only multiple electrodes each disposed on any one of the limbs.

The pulse measurement unit 140 measures a pulse wave of the user at the upper arm. In one example, the pulse wave measurement unit 140 includes a photoelectric sensor and measures a volume pulse wave with the photoelectric sensor. A known technique can be used as the method for measuring the pulse wave at the upper arm, and thus descriptions thereof will be omitted. The pulse measurement unit 140 outputs a pulse wave signal, which is a waveform signal indicating pulse wave fluctuation.

The determination unit 150 determines whether or not the user is in the relaxed state based on the pulse wave signal output from the pulse wave measurement unit 140. Specifically, the determination unit 150 calculates a peak interval, which is an interval between adjacent peaks, on the basis of the pulse wave signal and generates time series data for the peak interval. Next, the determination unit 150 calculates the power spectral density from the time series data of the peak interval using the autoregressive model, calculates the integrated value of power over the frequency range from 0.05 Hz to 0.15 Hz as LF, and calculates the integrated value of power over the frequency range from 0.15 Hz to 0.40 Hz as HF. The determination unit 150 determines that the user is in the relaxed state in a case where the LF/HF, which is the LF to HF ratio, is below a preset threshold, and determines that the user is not in the relaxed state in a case where the LF/HF is equal to or greater than the threshold.

Note that the determination unit 150 may calculate the heart rate on the basis of the pulse wave signal, and may determine that the user is in the relaxed state in a case where the calculated heart rate value is below a preset threshold and determine that the user is not in the relaxed state in a case where the calculated heart rate value exceeds the threshold.

The measurement control unit 151 controls the electrocardiographic measurement unit 130 and the pulse wave measurement unit 140. In response to the determination unit 150 determining that the user is in the relaxed state, the measurement control unit 151 controls the electrocardiographic measurement unit 130 to start measuring the electrocardiographic information. As an example, the measurement control unit 151 controls the pulse wave measurement unit 140 so as to periodically perform the measurement and, in response to the determination unit 150 determining that the user is in the relaxed state, controls the electrocardiographic measurement unit 130 to start measuring electrocardiographic information and, in response to the determination unit 150 determining that the user is not in the relaxed state, controls the electrocardiographic measurement unit 130 to stop measuring electrocardiographic information.

According to the electrocardiograph 100 having the configuration described above, the same effects as the electrocardiograph 10 illustrated in FIG. 1 can be obtained.

In short, the present invention is not limited to the embodiment described above as is, and the constituent elements can be modified and embodied within a range that does not depart from the gist in a stage of implementation. Further, various inventions can be formed by appropriately combining a plurality of constituent elements disclosed in the embodiment described above. For example, some constituent elements may be omitted from the entire constituent elements shown in the embodiment. Furthermore, the constituent elements of different embodiments may be combined appropriately.

Supplementary Notes

A part or the entirety of the embodiment can be described, as described in the following supplementary notes in addition to the scope of the claims, but the present invention is not limited thereto.

(Supplementary Note 1)

An electrocardiograph (10), including an electrocardiographic measurement unit (30) configured to measure electrocardiographic information of a user, a physiological indicator measurement unit (40) configured to measure a physiological indicator of the user, the physiological indicator being different from the electrocardiographic information, a first determination unit (50) configured to determine whether or not the user is in a relaxed state on the basis of a measurement result of the physiological indicator, and a measurement control unit (51) configured to control the electrocardiographic measurement unit on the basis of a determination result by the first determination unit.

Reference Signs List

- 10 Electrocardiograph
- 11 Control unit
- 12 CPU
- 13 RAM
- 14 ROM
- 15 Storage unit
- 16 Display device
- 17 Power button
- 18 Communication interface
- 19 Battery
- 20 Attachment member
- 21 Case
- 30 Electrocardiographic measurement unit
- 31, 32 Electrode
- 33 Signal processing circuit
- 331 Instrumentation amplifier
- 332 Low pass filter
- 333 Amplifier
- 334 Analog-to-digital converter
- 40 Respiration rate measurement unit
- 41 Acceleration sensor
- 42 Signal processing circuit
- 421 Low pass filter
- 422 Amplifier
- 423 Analog-to-digital converter
- 50 Determination unit
- 51 Measurement control unit
- 52 Electrocardiographic information acquisition unit
- 53 Respiration rate calculation unit
- 54 Communication control unit
- 55 Notification unit
- 57 Electrocardiographic information storage unit
- 61 First determination unit
- 62 Second determination unit
- 71 Detection unit
- 72 Notification unit
- 100 Electrocardiograph
- 120 Attachment member
- 130 Electrocardiographic measurement unit
- 140 Pulse wave measurement unit
- 150 Determination unit
- 151 Measurement control unit

The invention claimed is:

1. An electrocardiograph comprising:
   an electrocardiographic measurement unit including a pair of electrodes and a first circuit, the first circuit being configured to generate a potential difference signal indicating a potential difference between the electrodes and measure electrocardiographic information of a user based on the potential difference signal;
   a physiological indicator measurement unit including a sensor and a second circuit configured to measure a physiological indicator that is an indicator associated with a biological information of the user based on an output of the sensor, the physiological indicator being different from the electrocardiographic information; and
   a processor configured to:
      determine whether or not the user is in a relaxed state, on the basis of a measurement result of the physiological indicator;
      in response to a determination that the user is in the relaxed state, control the electrocardiographic measurement unit to start measuring the electrocardiographic information and control the physiological indicator measurement unit to stop measuring the physiological indicator;
      determine whether or not the user is in the relaxed state, on the basis of a measurement result of the electrocardiographic information during a period in which the electrocardiographic measurement unit measures the electrocardiographic information; and
      in response to a determination that the user is not in the relaxed state, control the electrocardiographic measurement unit to stop measuring the electrocardiographic information and control the physiological indicator measurement unit to perform measuring of the physiological indicator.

2. The electrocardiographic according to claim 1, wherein the physiological indicator is respiration rate, and
   the processor is configured to determine that the user is in the relaxed state in a case where the respiration rate is below a preset threshold and determine that the user is not in the relaxed state in a case where the respiration rate exceeds the preset threshold.

3. The electrocardiograph according to claim 2, wherein the processor is configured to, in response to a determination that the user is in the relaxed state, control the electrocardiographic measurement unit to start measuring the electrocardiographic information and, in response to a determination that the user is not in the relaxed state, control the electrocardiographic measurement unit to stop measuring the electrocardiographic information.

4. The electrocardiograph according to claim 2, wherein the processor is further configured to transmit a measurement result of the electrocardiographic information to an external device.

5. The electrocardiograph according to claim 2, wherein the processor is further configured to notify the user of a determination result of whether or not the user is in the relaxed state.

6. The electrocardiograph according to claim 3, wherein the processor is further configured to transmit a measurement result of the electrocardiographic information to an external device.

7. The electrocardiograph according to claim 1, wherein the processor is configured to, in response to a determination that the user is in the relaxed state, control the electrocardiographic measurement unit to start measuring the electrocardiographic information and, in response to a determination that the user is not in the relaxed state, control the electrocardiographic measurement unit to stop measuring the electrocardiographic information.

8. The electrocardiograph according to claim 7, wherein the processor is configured to control the physiological indicator measurement unit to continuously measure the physiological indicator in a time period in which the electrocardiographic measurement unit is not measuring the electrocardiographic information.

9. The electrocardiograph according to claim 7, wherein the processor is further configured to transmit a measurement result of the electrocardiographic information to an external device.

10. The electrocardiograph according to claim 7, wherein the processor is further configured to notify the user of a determination result of whether or not the user is in the relaxed state.

11. The electrocardiograph according to claim 8, wherein the processor is further configured to transmit a measurement result of the electrocardiographic information to an external device.

12. The electrocardiograph according to claim 8, wherein the processor is further configured to notify the user of a determination result of whether or not the user is in the relaxed state.

13. The electrocardiograph according to claim 1, wherein the processor is further configured to transmit a measurement result of the electrocardiographic information to an external device.

14. The electrocardiograph according to claim 1, wherein the processor is further configured to notify the user of a determination result of whether the user is in the relaxed state.

15. The electrocardiograph according to claim 1, wherein
   the physiological indicator measurement unit is configured to measure a plurality of types of physiological indicators of the user, the plurality of types of physiological indicators being different from the electrocardiographic information,
   the processor is configured to, in a case where it is determined that the user is not in the relaxed state, identify a type of physiological indicator, from among the plurality of types of physiological indicators, being the cause of determination that the user is not in the relaxed state, and
   the processor is configured to notify the user of the identified type of physiological indicator.

16. The electrocardiograph according to claim 1, wherein the physiological indicator includes at least one of respiration rate, pulse, heart rate, and pulse wave.

* * * * *